United States Patent

Rada

(10) Patent No.: US 8,394,047 B2
(45) Date of Patent: Mar. 12, 2013

(54) EXTRACORPOREAL BLOOD TREATMENT APPARATUS

(75) Inventor: Hiram Rada, Lyons (FR)

(73) Assignee: Gambro Lundia AB, Lund (SE)

( * ) Notice: Subject to any disclaimer, the term of this patent is extended or adjusted under 35 U.S.C. 154(b) by 33 days.

(21) Appl. No.: 13/196,009

(22) Filed: Aug. 2, 2011

(65) Prior Publication Data

US 2012/0029409 A1     Feb. 2, 2012

(30) Foreign Application Priority Data

Aug. 2, 2010   (EP) ................................. 10008037

(51) Int. Cl.
*A61M 37/00* (2006.01)

(52) U.S. Cl. .................... 604/6.09; 604/6.11; 604/6.05

(58) Field of Classification Search .................. 604/4.01, 604/6.05, 6.09
See application file for complete search history.

(56) References Cited

U.S. PATENT DOCUMENTS

| | | | |
|---|---|---|---|
| 4,231,366 A | 11/1980 | Schael | |
| 4,464,164 A | 8/1984 | Troutner et al. | |
| 4,490,135 A * | 12/1984 | Troutner | 604/6.05 |
| 4,498,983 A | 2/1985 | Bilstad et al. | |
| 4,758,336 A | 7/1988 | Bock | |
| 5,098,373 A * | 3/1992 | Polaschegg | 604/6.05 |
| 5,227,049 A | 7/1993 | Chevallet | |
| 7,540,958 B2 * | 6/2009 | Chevallet et al. | 210/258 |
| 2011/0178452 A1 | 7/2011 | Kopperschmidt | |

FOREIGN PATENT DOCUMENTS

| | | |
|---|---|---|
| EP | 0 229 271 A2 | 7/1987 |
| EP | 0 229 271 A3 | 10/1987 |
| EP | 0 229 271 B1 | 8/1990 |
| EP | 0 472 480 A1 | 2/1992 |
| EP | 0 472 480 B1 | 8/1995 |
| WO | WO 2008/148505 A2 | 12/2008 |
| WO | WO 2008/148505 A3 | 6/2009 |
| WO | WO 2010/037520 A1 | 4/2010 |

* cited by examiner

*Primary Examiner* — Leslie Deak
*Assistant Examiner* — Jordan B Bailey
(74) *Attorney, Agent, or Firm* — Mueting Raasch & Gebhardt PA

(57) ABSTRACT

In a single needle extracorporeal blood treatment apparatus, an ultrafiltration pump (10) performs a pure ultrafiltration of ultrafiltrate from an hemofilter (4). The blood may be continuously circulated through the hemofilter using a first pump (5), which alternates an higher flow rate during the arterial phase and a lower flow rate during the venous phase, and a second pump (6) which is maintained at a flow rate intermediate between said higher and lower flow rate. The apparatus may be used for treatment of Congestive Heart Failure.

20 Claims, 3 Drawing Sheets

Fig. 3
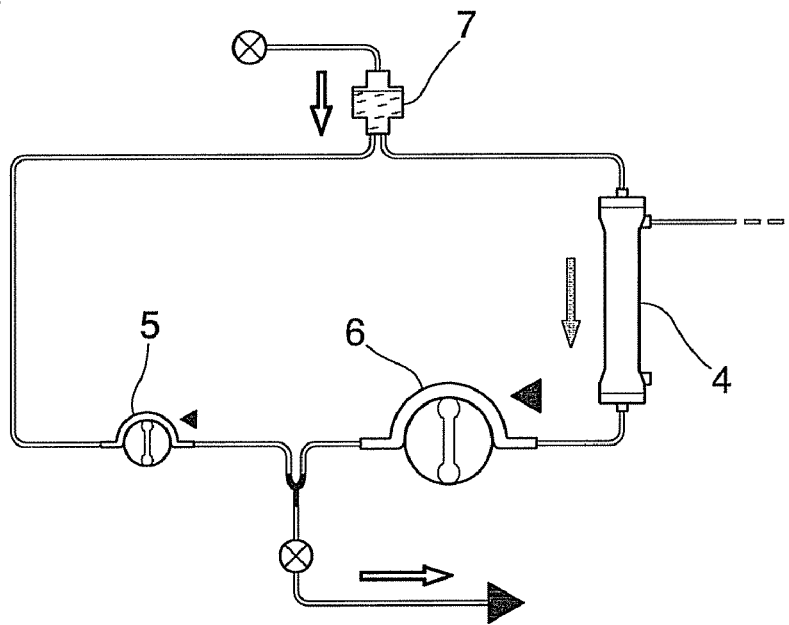
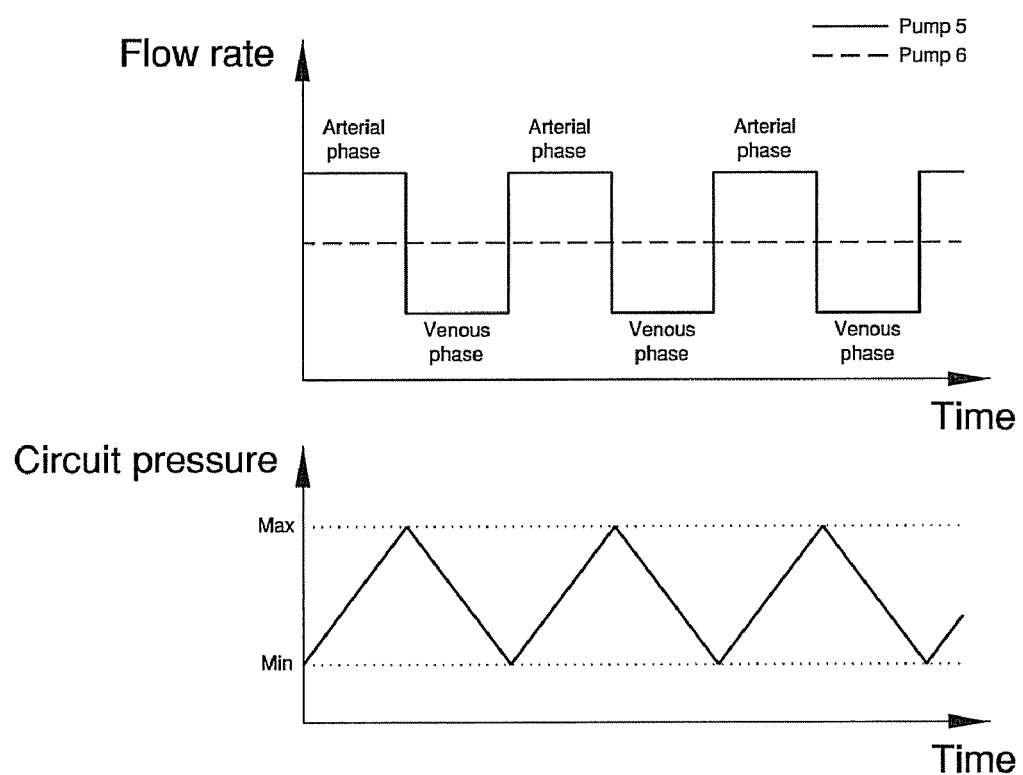
Fig. 4

EXTRACORPOREAL BLOOD TREATMENT APPARATUS

TECHNICAL FIELD

Extracorporeal blood treatment apparatus are described herein which may be advantageously usable in the treatment of, e.g., CHF (Congestive Heart Failure).

BACKGROUND

As is known, the treatment of congestive heart failure by a CI-IF apparatus consists of removing patient fluid overload by means of pure ultrafiltration. Fluid removal therapy is commonly referred to as SCUF (Slow Continuous Ultra-Filtration) and is basically performed by means of an extracorporeal blood circuit including a hemofilter, an anticoagulation means (syringe pump), a fluid removal device (e.g. roller pump) and safety devices (air and blood leak detectors, pressure sensors, patient sensor).

Moreover it is known to perform extracorporeal blood treatments (such as hemodialysis, hemodiafiltration, hemoperfusion, etc.) by means of blood circuits of the single needle type, in which blood is withdrawn from, and returned to, the patient's circulatory system through a single needle with a Y-shaped junction. In these circuits, blood may be alternately cycled from and to the patient's body by a single blood pump, or by arterial and venous blood pumps, respectively. During a first (withdrawal or arterial) phase of operation, blood is drawn from the patient and pumped into the treatment device (exchanger of a semipermeable membrane type) by the arterial blood pump. Blood is prevented from returning to the needle by the closure of a valve (clamp) located between the outlet of the arterial pump and the needle, or through a clamping action of the venous blood pump. Blood pressure within the blood circuit builds until a time at which the arterial pump is turned off, the valve is opened, or the venous pump in a two-pump system is turned on to pump the blood out of the treatment device and back to the patient during a second (return or venous) phase of operation. After the return of a desired amount of blood to the patient, the venous phase is terminated and the cycle repeats. The single needle system has the advantage of half the number of needle insertions, which may be psychologically attractive to the patient, as well as prolonging the life of the fistula into which the needle is normally inserted.

U.S. Pat. No. 4,231,366 discloses a single needle system used in connection with such treatments as blood dialysis, blood perfusion and blood diafiltration, in which an arterial blood pump operates during the blood withdrawal phase as well as during the blood return phase, whereas a venous blood pump only operates during the blood return phase with a pumping rate which is larger than the rate of the arterial pump. The return blood flow pumped by the venous pump is divided in the junction member so that a proportion is returned to the patient through the needle and another proportion is pumped again by the arterial pump in accordance with the pumping rate of the arterial pump, whereby the blood is subjected repeatedly to a cleaning operation in the treatment device.

SUMMARY

An aim of the apparatus described herein is to provide an apparatus which is able to perform a fluid removal therapy in a single needle mode.

A potential aim of the apparatus and methods described herein is to make available a mode, particularly a single-needle mode, which is simpler than existing modes in order to perform a pure ultrafiltration blood treatment.

A potential advantage is achieving continuous blood circulation in the hemofilter (membrane device in which the pure ultrafiltration occurs) and avoiding excessive hemoconcentration therein.

Another potential advantage is reducing the noise during the treatment of pure ultrafiltration, particularly by avoiding the use of one or more clamps to block the blood flow in predefined portions of the extracorporeal blood circuit.

A further potential advantage is minimizing the extracorporeal blood volume of the blood circuit so as to perform a blood treatment (pure ultrafiltration) with a small extracorporeal blood volume.

A further potential advantage is to provide an extracorporeal blood treatment apparatus having an easy setup.

Additionally, other potential advantages are to realise an apparatus which can be extremely simple and reliable and which can provided with an easy to use user interface.

At least one of the above-indicated aims and advantages, which will better emerge during the course of the present description, are preferably attained by an apparatus for extracorporeal blood treatment according to what is described in the appended claims, taken singly or in any combination.

Further characteristics and advantages will better emerge from the detailed description that follows of a non-exclusive embodiment of an apparatus as described herein.

BRIEF DESCRIPTION OF THE DRAWINGS

The description will be made with reference to the accompanying figures of the drawings, provided by way of non-limiting example.

FIG. 3 shows the apparatus of FIG. 1 in the return, or venous, phase operation wherein the flow rate of pump 1 is lower than that of pump 2.

FIG. 4 shows a graph of flow rates of pump 1 and pump 2 and a graph of the corresponding variations in circuit pressure which trigger the switch between arterial and venous phases.

DETAILED DESCRIPTION

Figure 1:
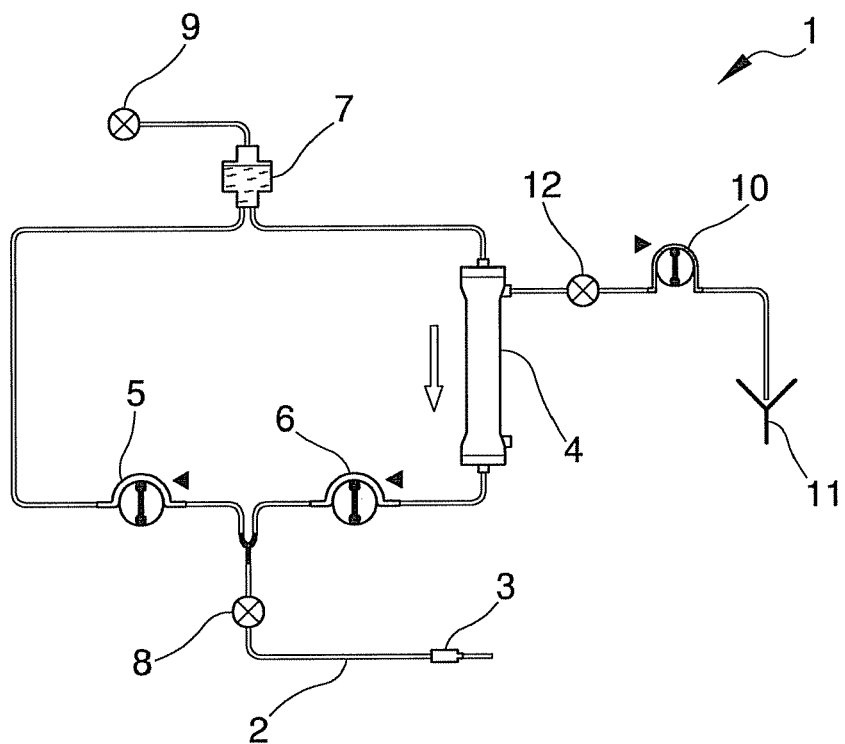
FIG. 1 is a schematic illustration of one illustrative embodiment of a single-needle apparatus for ultrafiltration.
Figure 2:
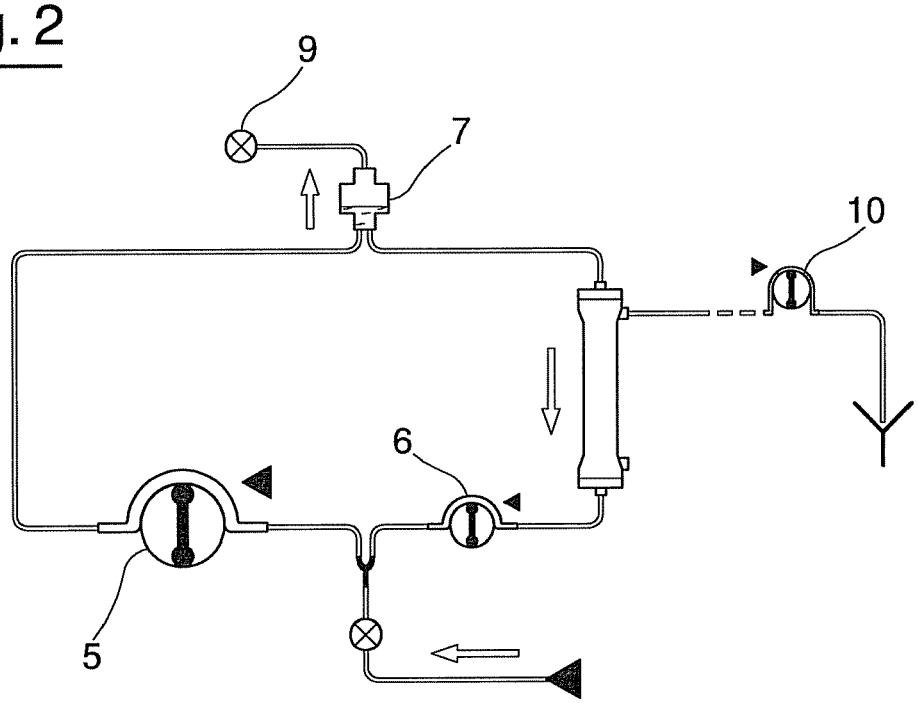
FIG. 2 shows the apparatus of FIG. 1 in the withdrawal, or arterial, phase operation wherein the difference in size between pumps 1 and 2 is used to represent the difference in flow rate.

With reference to FIGS. 1 to 3 of the drawings, 1 denotes in its entirety an extracorporeal blood treatment apparatus configured to perform a fluid removal treatment (ultrafiltration-only treatment), in particular for the treatment of CHF (Congestive Heart Failure).

It is thus described a single-needle blood circuit intended to be used for performing pure ultrafiltration treatments (e.g. for treatment of CHF) where the primary goal is the achievement of water removal rather than solute removal.

The apparatus 1 comprises a single-needle extracorporeal blood circuit. The blood circuit comprises a patient line 2 connected, in a known manner, to the single needle 3. The patient line 2 has a three way junction, of known type (e.g. T-junction or Y-junction), for the connection to a first (arterial or withdrawal) line and a second (venous or return) line. The patient line 2 and the first and second lines are configured to transport the blood. The direction of the blood flow is indicated by an arrow. The first line connects the patient line 2 to an inlet of a first chamber of a semipermeable membrane device 4 (e.g. hemofilter) in which the blood treatment (pure ultrafiltration) will occur. The second line connects the patient line to an outlet of the first chamber of the membrane device 4. The membrane device 4 has a semipermeable membrane which separates the first chamber from a second chamber.

The apparatus 1 comprises blood circulating means which, in the depicted embodiment, comprises a first blood pump 5 arranged on the first line and a second blood pump 6 arranged on the second line. The blood pumps 5 and 6 may be of the occlusive type (e.g. peristaltic pumps).

The apparatus 1 comprises an expansion chamber 7 arranged on the first line. The expansion chamber 7 constitutes a compliance of the single-needle blood circuit. The volume of the expansion chamber 7 is preferably significantly higher than the volume of the access line 2 between the junction and the needle 3.

In the depicted single needle blood circuit only one expansion chamber 7 is provided so as to limit the blood withdrawn from the patient circulating in the extracorporeal circuit.

The apparatus 1 comprises a first pressure measurement device 8 arranged to measure the pressure in a region of the blood circuit comprised between the needle 3 and the blood pumps 5 and 6. The first pressure measurement device 8 may be connected to the patient line 2; alternatively the pressure sensor 8 may be connected either between the Y junction and blood pump 5 or between the Y junction and blood pump 6. The apparatus 1 comprises a second pressure measurement device 9 arranged to measure the pressure in a further region of the blood circuit comprised between the blood pumps 5 and 6 and including the membrane device 4. The second pressure measurement device 9 may be connected to the first line. The second pressure measurement device 9 may be connected to the expansion chamber 7. The pressure measurement devices 8 and 9 measure the pressure of the blood access proximal to the needle 3 and, respectively, the pressure inside the blood circuit proximal to the membrane device 4.

The apparatus 1 comprises an ultrafiltration circuit, of known type, which comprises an ultrafiltration line connected to an outlet of the second chamber of the membrane device 4. The ultrafiltration circuit comprises an ultrafiltration pump 10 which provides the circulation of the fluid (ultrafiltrate) removed from the blood. The flow of the removed fluid goes from the outlet of the second chamber of the membrane device 4 to a drain 11. The ultrafiltration circuit comprises an ultrafiltration pressure measurement device 12 arranged to measure the pressure in the ultrafiltration line between the membrane device 4 and the ultrafiltration pump 10.

The apparatus comprises a control unit which is connected to the actuators (pumps 5, 6, 10) and the sensors (pressure measurement devices 8, 9, 12) of the apparatus in order to control the operation thereof. The control unit is configured to operate according to a predefined (software) program which comprises the instructions to perform the extracorporeal blood treatment method as below explained.

As is known, the operation of a single-needle extracorporeal blood circuit is achieved by alternatively switching from an arterial phase (during which the blood in withdrawn from the blood access) to a venous phase (during which the blood is returned to the patient).

FIG. 2 illustrates the operation during the arterial phase.

The arterial phase is achieved by setting the flow rate of the first pump 5 higher than the flow rate of the second pump 6. The difference between the two flow rates results in a flow rate of blood coming from the patient. During the arterial phase the level of blood in the expansion chamber 7 increases and results in an increase of the pressure in the blood circuit as measured by the second pressure measurement device 9.

The switch to the venous phase is triggered when the pressure measured by the second pressure measurement device 9 reaches a pre-determined threshold value.

During the arterial phase the blood flow in the membrane device 4 (from the inlet to the outlet of the first chamber of the membrane device 4) is substantially equal to the flow rate of the second pump 6 (neglecting the ultrafiltration flow rate actuated by the ultrafiltration pump 10 through the membrane of the membrane device 4).

FIG. 3 illustrates the operation during the venous phase.

During the venous phase the flow rate of the first pump 5 is set lower than the flow rate of the second pump 6.

This results in returning blood to the patient at a rate equal to the difference between the flow rates of the pumps 6 and 5. The blood level in the expansion chamber 7 decreases as well as the pressure in the blood circuit measured by the second pressure measurement device 9. The venous phase ends when the pressure measured by the second pressure measurement device 9 decreases below a pre-determined threshold value.

During the venous phase the flow rate in the membrane device 4 (from the inlet to the outlet of the first chamber of the membrane device 4) is substantially equal to the flow rate of the pump 6 (neglecting the ultrafiltration flow rate).

FIG. 4 gives a representation of the alternation of the two pump flow rates between the arterial phase and the venous phase and the corresponding variations in the blood circuit pressure (the pressure measured by the second pressure measurement device 9).

According to the embodiment above described, the switch between the arterial phase and the venous phase may be triggered by using pressure signals, in particular when the maximum and minimum threshold pressures are reached.

According to another embodiment, a level detector operatively connected to the expansion chamber 7 may be used to trigger the switching from one phase to another phase. In particular the control unit may be programmed to switch between the two phases when maximum and minimum threshold blood levels in the expansion chamber 7 are reached.

Figure 5:
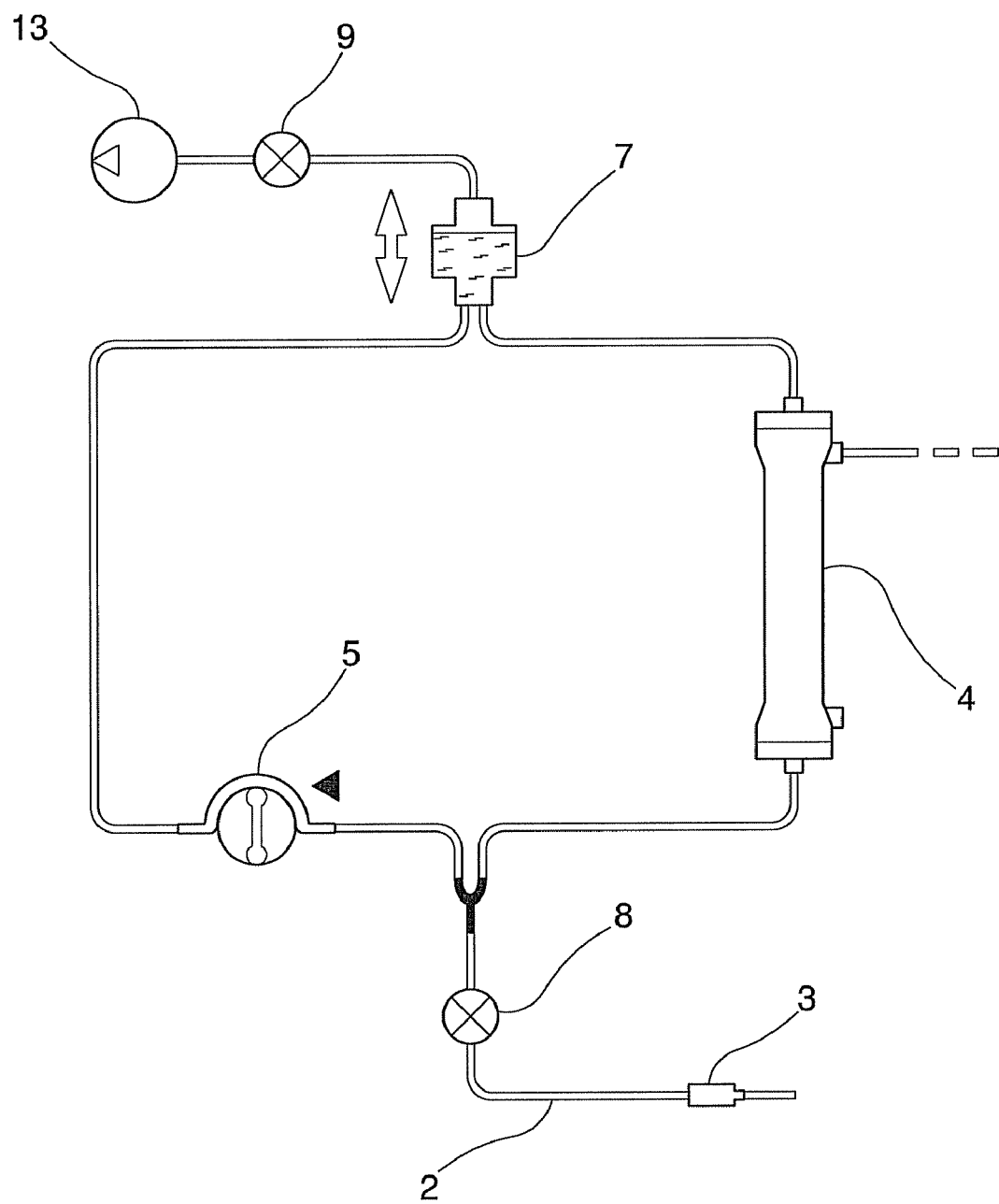
FIG. 5 is a possible further embodiment of the single-needle apparatus for ultrafiltration wherein one pump on the blood circuit and a gas (e.g., air) pump are used.

FIG. 5 shows an alternative single needle blood treatment apparatus which achieves the single-needle functionality in a different manner. The ultrafiltration circuit may be the same as in the apparatus of FIG. 1. The same elements of the apparatus of FIG. 1 have been indicated with the same numeral reference. The apparatus of FIG. 5 will be provided with a control unit as for the apparatus of FIG. 1.

The apparatus of FIG. 5 comprises a gas (e.g., air) pump 13 connected to the expansion chamber 7. The pump 13 may replace one of two pumps 5 or 6 of the apparatus of FIG. 1. In the specific embodiment of FIG. 5 the first pump 5 (upstream from the membrane device 4) is present and the second pump 6 (downstream from the membrane device 4) is absent. The second pump 6 has been functionally replaced by the gas (e.g., air) pump 13 operating on the expansion chamber 7. In another embodiment (not shown) the first pump 5 (upstream from the membrane device 4) may be absent (functionally replaced by the pump 13 operating on the expansion chamber 7) and the second pump 6 (downstream the membrane device 4) may be present.

The blood pump that is present (the first pump 5 in FIG. 5) will operate to ensure the continuous circulation of the blood in the blood circuit. The gas (e.g., air) pump 13 may alternately operate in both directions so as to alternately empty and fill the expansion chamber 7. The pump 13 will operate to control the blood level in the expansion chamber 7.

The pump 13 allows to alternate the arterial phase and the venous phase by alternatively emptying and filling the expansion chamber 7. The control of the pump 13, as well as of the first pump 5) may be based on information on the situation in the expansion chamber 7. In particular the pump 13 may be controlled on the basis of pressure signals received from the second pressure measurement device 9, or on the basis of blood level signals received from a blood level sensor associated to the expansion chamber 7. The first pump 5 may be controlled so as to pump an arterial flow rate during the arterial phase and a venous flow rate during the venous phase, in which the arterial flow rate is higher than the venous flow rate. The first pump 5 and the pump 13 maybe controlled so as to maintain substantially the same flow rate in the first chamber of the membrane device 4 both in the arterial and in the venous phase.

According to other embodiments not shown, the (arterial) expansion chamber 7 of FIGS. 1 and 5 may be arranged in the second (venous) line. In a first case, analogous to the case of FIG. 1, the (venous) expansion chamber will be arranged upstream from the second pump 6 (between the device 4 and the pump 6), and in a second case, analogous to the case of FIG. 5, the (venous) expansion chamber will be operatively associated to gas (e.g., air) pump as the pump 13 and, optionally, to a pressure measurement device as the device 9. In the first case, the first pump 5 may operate at a constant rate while the second pump 6 may alternate a withdrawal phase at a less rate than the first pump 5 and a return phase at a greater rate than the first pump 5. In the second case, the first pump 5 may operate at, e.g., a constant rate while the reversal of pump may alternate a withdrawal phase at a predefined rate in a suction mode (in which, e.g., a gas such as air is removed from the expansion chamber) and a return phase at a predefined rate in a pumping mode (in which, e.g., a gas such as air is pumped into the expansion chamber).

In the extracorporeal blood circuits of the above embodiments the first line and the second line are configured so that during the withdrawal phase and during the return phase the blood flow in the second line can freely and partially recirculate into the first line through the three-way junction. In particular, blood flow is not blocked by any clamps or other clamp means that may be provided in the first line between the first pump 5 and the three way junction and/or in the second line between the second pump 6 or 13 and the three way junction.

The extracorporeal blood treatment apparatus may be provided with means, of known type, for anticoagulation of the blood.

An air bubble detector may be placed downstream the membrane device 4 to detect the dangerous presence of air bubbles in the blood and, in such a case, putting the apparatus in safe condition for the patient.

It is finally to be noted that a blood leak detector might be associated to the ultrafiltration circuit, for example before or after the pressure device 12.

Also described is a method that may include:
providing a membrane device 4 having a first chamber, a second chamber and a semipermeable membrane separating said first chamber from said second chamber;
providing a single needle extracorporeal blood circuit having a three way junction connecting a patient line 2, a first line and a second line, said single needle extracorporeal blood circuit having an expansion chamber 7;
connecting said patient line 2 to a patient vascular access;
connecting said first line to an inlet of said first chamber;
connecting said second line to an outlet of said first chamber;
connecting a first pump 5 and a second pump 6; 13 to said single needle extracorporeal blood circuit to circulate a blood flow therein;
connecting an ultrafiltration device to said second chamber;
controlling said first and second pumps and said ultrafiltration device, said controlling comprising: alternating a withdrawal phase in which blood is withdrawn from said patient vascular access through said patient line 2 and a return phase in which blood is returned to said patient vascular access through said patient line 2, operating both said first and second pumps during said withdrawal phase so as to recirculate a fraction of blood flow from said second line to said first line through said three way junction, and operating said ultrafiltration device so as to perform a pure ultrafiltration treatment during said recirculation.

The method may further comprise one or more of the following actions, in any combination thereof: no clamp is operated to block blood flow in said first line between said first pump 5 and said three way junction and/or said second line between said second pump 6; 13 and said three way junction; connecting said first pump 5 to said first line and said second pump 6 to said second line, arranging said expansion chamber 7 downstream said first pump 5 and upstream said second pump 6, and controlling said first pump at a flow rate higher than a flow rate of said second pump during said withdrawal phase and less than a flow rate of said second pump during said return phase; controlling said second pump 6 at a same (in some embodiments, constant) flow rate during said withdrawal and return phases; connecting said second pump, which comprises a gas (e.g., air) pump 13, to said expansion chamber 7, controlling said pump so as to remove gas (e.g., air) from said expansion chamber 7 during said withdrawal phase and to pump gas (e.g., air) into said expansion chamber 7 during said return phase; connecting said first pump 5 to said first line, connecting said expansion chamber 7 to said first line downstream said first pump 5, controlling said first pump 5 at a flow rate during said withdrawal phase that is higher than a flow rate during said return phase; connecting said first pump 5 to said first line, connecting said expansion chamber 7 to said second line, controlling said first pump 5 at a same (in some embodiments, constant) flow rate during said withdrawal and return phases; controlling at least one or both of said first and second pumps at flow rates not equal to zero during both said withdrawal and said return phases; connecting three pressure measurement devices 8; 9; 12, respectively, to said patient line 2, to said expansion chamber 7, and to said second chamber; triggering a switch between said withdrawal phase and said return phase on the basis of pressure signals indicative of the pressure in said expansion chamber.

The membrane device, the extracorporeal blood circuit and the ultrafiltration line may be configured to form a single disposable unit.

The invention claimed is:
1. Extracorporeal blood treatment apparatus comprising:
a membrane device having a first chamber, a second chamber and a semipermeable membrane separating said first chamber from said second chamber;
a single needle extracorporeal blood circuit having a three way junction connecting a patient line, a first line and a second line, said patient line being connectable to a patient vascular access, said first line being connected to an inlet of said first chamber, said second line being connected to an outlet of said first chamber, said single needle extracorporeal blood circuit being provided with an expansion chamber;

a first pump and a second pump configured to circulate a blood flow in said single needle extracorporeal blood circuit;

an ultrafiltration device operatively connected to said second chamber;

a control unit configured to control said first and second pumps to circulate a blood flow in said single needle extracorporeal blood circuit and to control said ultrafiltration device to perform a pure ultrafiltration of ultrafiltrate from said blood flow through said semipermeable membrane, said controller configured to control said first and second pumps so as to alternate a withdrawal phase in which blood is withdrawn from said patient vascular access through said patient line and a return phase in which blood is returned to said patient vascular access through said patient line, wherein said controller is configured to operate both said first and second pumps during said withdrawal phase so as to recirculate a fraction of blood flow from said second line to said first line through said three way junction and said controller is further configured to control said first pump at a flow rate higher than a flow rate of said second pump during said withdrawal phase and less than a flow rate of said second pump during said return phase, and wherein said controller is configured to operate said ultrafiltration device so as to perform a pure ultrafiltration treatment during said recirculation.

2. The apparatus of claim 1, wherein no clamp is provided to block blood flow in said first line between said first pump and said three way junction or in said second line between said second pump and said three way junction.

3. The apparatus of claim 1, wherein said first pump is arranged on said first line and said second pump is arranged on said second line, said expansion chamber being arranged downstream from said first pump and upstream from said second pump.

4. The apparatus of claim 3, wherein said expansion chamber is arranged in said first line, said controller configured to control said second pump at a same flow rate during said withdrawal and return phases.

5. The apparatus of claim 3, wherein said expansion chamber is arranged in said second line, said controller configured to control said first pump at a same flow rate during said withdrawal and return phases.

6. The apparatus of claim 1, wherein said second pump comprises a gas pump connected to said expansion chamber, said controller configured to control said gas pump so as to remove gas from said expansion chamber during said withdrawal phase and to pump gas into said expansion chamber during said return phase.

7. The apparatus of claim 6, wherein said first pump is arranged on said first line, said expansion chamber being arranged in said first line downstream from said first pump, said controller configured to control said first pump at a flow rate during said withdrawal phase that is higher than a flow rate during said return phase.

8. The apparatus of claim 6, wherein said first pump is arranged on said first line, said expansion chamber being arranged in said second line, said controller configured to control said first pump at a same flow rate during said withdrawal and return phases.

9. The apparatus of claim 1, wherein said expansion chamber is arranged in said first line.

10. The apparatus of claim 1, wherein said controller is configured to control at least one of said first and second pumps at flow rates greater than zero during both said withdrawal and said return phases.

11. The apparatus of claim 1, comprising three pressure measurement devices, wherein one of said three pressure measurement devices is connected to said patient line, one of said three pressure measurement devices is connected to said expansion chamber, and one of said three pressure measurement devices is connected to said second chamber.

12. The apparatus of claim 1, wherein said controller is configured to switch between said withdrawal and return phases on the basis of pressure signals indicative of the pressure in said expansion chamber.

13. The apparatus of claim 1, wherein one of said first pump and second pump are pumps of the occlusive type.

14. The apparatus of claim 1, wherein the single needle extracorporeal blood circuit has only one expansion chamber.

15. Extracorporeal blood treatment apparatus comprising:
a membrane device having a first chamber, a second chamber and a semipermeable membrane separating said first chamber from said second chamber;
a single needle extracorporeal blood circuit having a three way junction connecting a patient line, a first line and a second line, said patient line being connectable to a patient vascular access, said first line being connected to an inlet of said first chamber, said second line being connected to an outlet of said first chamber, said single needle extracorporeal blood circuit being provided with an expansion chamber;
a first pump and a second pump configured to circulate a blood flow in said single needle extracorporeal blood circuit; said second pump comprising a gas pump connected to said expansion chamber,
an ultrafiltration device operatively connected to said second chamber;
a control unit configured to control said first and second pumps to circulate a blood flow in said single needle extracorporeal blood circuit and to control said ultrafiltration device to perform a pure ultrafiltration of ultrafiltrate from said blood flow through said semipermeable membrane, said controller configured to control said first and second pumps so as to alternate a withdrawal phase in which blood is withdrawn from said patient vascular access through said patient line and a return phase in which blood is returned to said patient vascular access through said patient line, wherein said controller is configured to operate both of said first and second pumps during said withdrawal phase so as to recirculate a fraction of blood flow from said second line to said first line through said three way junction, and wherein said controller is configured to operate said ultrafiltration device so as to perform a pure ultrafiltration treatment during said recirculation, wherein said controller is configured to control said gas pump so as to remove gas from said expansion chamber during said withdrawal phase and to pump gas into said expansion chamber during said return phase.

16. The apparatus of claim 15, wherein said controller is configured to switch between said withdrawal and return phases on the basis of pressure signals indicative of the pressure in said expansion chamber.

17. The apparatus of claim 16, wherein said first pump is arranged on said first line, said expansion chamber being arranged in said first line downstream from said first pump, said controller configured to control said first pump at a flow rate during said withdrawal phase that is higher than a flow rate during said return phase.

18. The apparatus of claim 16, wherein said first pump is arranged on said first line, said expansion chamber being arranged in said second line, said controller configured to control said first pump at a same flow rate during said withdrawal and return phases.

19. The apparatus of claim 15, wherein said controller is configured to control at least one of said first and second pumps at flow rates greater than zero during both said withdrawal and said return phases.

20. The apparatus of claim 15, comprising three pressure measurement devices, wherein one of said three pressure measurement devices is connected to said patient line, one of said three pressure measurement devices is connected to said expansion chamber, and one of said three pressure measurement devices is connected to said second chamber.

* * * * *